United States Patent [19]
Szántay et al.

[11] 4,428,877
[45] * Jan. 31, 1984

[54] CIS-10-BROMO-E-HOMOEBURNANES

[75] Inventors: Csaba Szántay; Lajos Szabó; György Kalaus; Lajos Dancsi; Tibor Keve; Egon Kárpáti; László Szporny, all of Budapest, Hungary

[73] Assignee: Richter Gedeon Vegyeszeti Gyar Rt., Budapest, Hungary

[*] Notice: The portion of the term of this patent subsequent to Feb. 9, 1999 has been disclaimed.

[21] Appl. No.: 234,577

[22] Filed: Feb. 13, 1981

Related U.S. Application Data

[62] Division of Ser. No. 56,395, Jul. 10, 1979, Pat. No. 4,315,011.

[30] Foreign Application Priority Data

Jul. 12, 1978 [HU] Hungary ................. RI 672
Jul. 12, 1978 [HU] Hungary ................. RI 673
Jul. 12, 1978 [HU] Hungary ................. RI 674
Jul. 12, 1978 [HU] Hungary ................. RI 675

[51] Int. Cl.³ .................. C07D 459/00; C07D 471/22
[52] U.S. Cl. .................. 260/244.4; 424/262
[58] Field of Search .................. 260/244.4, 239.3 P

[56] References Cited

U.S. PATENT DOCUMENTS 3,770,724 11/1973 Warnat et al. ............... 260/239.3 P
4,138,489 2/1979 Thal et al. ................... 546/70
4,146,643 3/1979 Pfaffli ........................ 546/70
4,283,401 8/1981 Szantay et al. ............. 546/70

FOREIGN PATENT DOCUMENTS 2478639 4/1981 France .................. 546/70

Primary Examiner—Paul M. Coughlan, Jr.
Assistant Examiner—D. B. Springer
Attorney, Agent, or Firm—Karl F. Ross; Herbert Dubno

[57] ABSTRACT

A novel process for preparing 10-bromo-vincaminic acid esters and homologous compounds of the general formula wherein $R^1$ and $R^2$ each stand for a $C_{1-6}$ alkyl group is disclosed.

6 Claims, No Drawings

CIS-10-BROMO-E-HOMOEBURNANES

This is a division of application Ser. No. 056,395, filed July 10, 1979, now U.S. Pat. No. 4,315,011 filed on Feb. 9, 1982.

This invention relates to a novel process for the preparation of racemic or optically active 10-bromovincaminic acid esters of formula (I), (I)

wherein $R^1$ and $R^2$ are each $C_{1-6}$ alkyl group, and pharmaceutically acceptable acid addition salts thereof.

These compounds are prepared according to the invention as follows:

(a) p-halo-aniline of formula (II), (II)

is subjected to diazotization, the resulting diazonium salt is reacted with a malonate compound of formula (III), $$\begin{array}{c} COOR^4 \\ | \\ CH-CH_2-CH_2-CH_2-Y \\ | \\ COOR^4 \end{array}$$ (III)

wherein $R^4$ is an alkyl group of 1 to 6 carbon atoms and Y stands for halogen, in an alkaline medium, the resulting phenylhydrazone derivative of formula (IV), $$\begin{array}{c} COOR^4 \\ | \\ C-CH_2-CH_2-CH_2-Y \\ \| \\ N \\ | \\ NH-\!\!\!\bigcirc\!\!\!-Br \end{array}$$ (IV)

wherein $R^4$ and Y are as defined above, is subjected to ring closure, the resulting 5-bromo-tryptaminecarboxylic acid ester of formula (V)

(V)

wherein $R^4$ and Y are as defined above, is subjected to hydrolysis in an alkaline medium and the resulting 5-bromo-tryptaminecarboxylic acid of the formula (Va)

(Va)

is decarboxylated in an acidic medium, or the ester of formula (V) is hydrolyzed and decarboxylated in one step in an acidic medium, the resulting 5-bromotryptamine of formula (VI), (VI)

is reacted, optionally after converting it into an acid addition salt, with a pentanolide derivative of formula (VII), (VII)

wherein $R^2$ is as defined above, the resulting valeroyltryptamine derivative of formula (VIII)

(VIII)

wherein $R^2$ is as defined above, is subjected to ring closure, the resulting product is converted into its acid addition salt, the obtained 9-bromo-1-alkyl-hexahydroindoloquinolizinium salt of formula (IX), (IX)

wherein $R^2$ is as defined above and $A^\ominus$ represents the anion of an acid, is reacted with a base and then with an acrylate of formula (X), $$R^3O-\underset{\underset{O}{\|}}{C}-CH\!=\!CH_2$$ (X)

wherein $R^3$ is a $C_{1-6}$ alkyl group, or (b) a 1-alkyl-hexahydro-indoloquinolizinium salt of formula (XI),

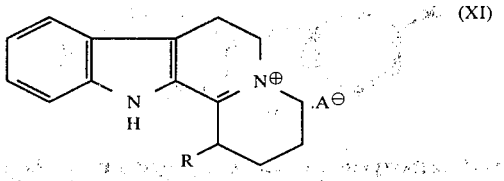
(XI)

wherein R and A⊖ are as defined above, is reacted with a brominating agent, the obtained 9-bromo-1-alkyl-hexa-hydroindoloquinolizinium salt of formula (IX),

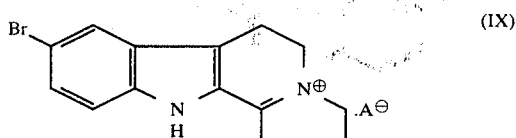
(IX)

wherein R² is as defined above and A⊖ represents the anion of an acid, is reacted with a base and then with an acrylate of formula (X),

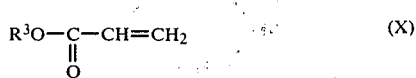
(X)

wherein R³ is a C₁₋₆ alkyl group, or (c) a 1-alkyl-1-alkoxycarbonylethyl-hexahydro-indoloquinolizinium salt of formula (XII),

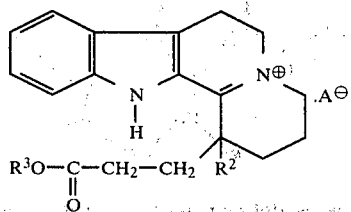
(XII)

wherein R², R³ and A⊖ are as defined above, is treated with a brominating agent, and the double bond appearing between rings C and D of the resulting oily 1-ethyl-1-alkoxycarbonylethyl-9-halo-hexahydroindolo-quinolizine derivative is reduced selectively either by reducing this compound itself or by reacting it first with an alcohol of formula R⁵-OH, wherein R⁵ is C₁₋₆ alkyl, optionally converting the resulting compound of formula (XIIIa),

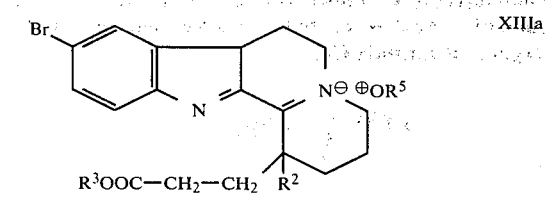
XIIIa wherein R², R³ and R⁴ are as defined above, into an acid addition salt of formula (XIIIb),

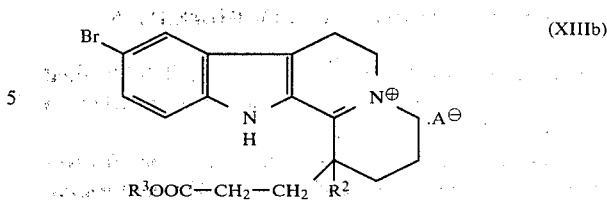
(XIIIb)

wherein R², R³ and A⊖ are as defined above, and reducing the resulting alkoxide or salt, the individual components of the resulting isomeric mixture containing 1-alkyl-1-alkoxy-carbonylethyl-9-bromo-octahydroin-doloquinolizine isomers of formulae (XIVa) and (XIVb),

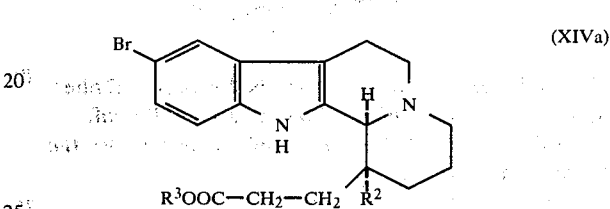
(XIVa)

(XIVb)

wherein R² and R³ are as defined above, are separated from each other, the resulting 1 α-alkyl-1β-alkoxycar-bonyl-ethyl-9-bromo-12b α H-octahydroindoloquinoli-zine of formula (XIVa), wherein R² and R³ are as defined above, or an acid addition salt thereof is treated with an alkaline agent, the resulting 10-bromo-14-oxo-E-homo-eburnane derivative of formula (XV),

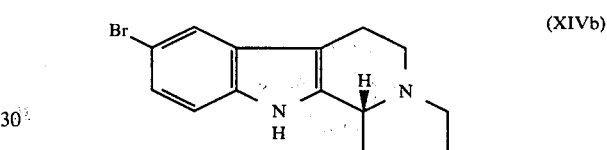
(XV)

wherein R² is as defined above, is reacted with a nitrosating agent, the resulting 10-bromo-14-oxo-15-hydroxyimino-E-homo-eburnane derivative of formula (XVI),

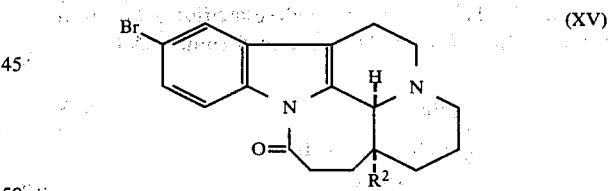
(XVI)

wherein R² is as defined above, is subjected to deoxyimination, and the resulting 10-bromo-14,15-dioxo-E-homo-eburnane derivative of formula (XVII),

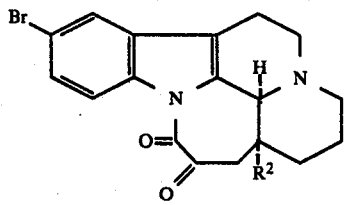

(XVII)

wherein R² is as defined above, is treated with a base in an alcohol of formula R¹OH, wherein R¹ is as defined above, and if desired, a racemic end-product of formula (I) is resolved in a manner known per se to yield the pure optically active isomers, or, if desired, the optically active compounds of formula are prepared by resolving any of the racemic intermediates formulae (Va), (VI), (VII), (IX), (XI), (XII), (XIIIa), (XIIIb), (XIVa), (XIVb), (XV), (XVI) or (XVII), and performing the subsequent reaction step(s) with the respective optically active intermediate. If desired, the free bases of formula (I) can be converted into their pharmaceutically acceptable acid addition salts.

In the above formulae R¹ and R² can be straight-chain or branched $C_{1-6}$ alkyl, such as methyl, ethyl, n-propyl, isopropyl, n-butyl, isobutyl, sec.-butyl, tert.-butyl, n-pentyl, isopentyl, n-hexyl and isohexyl.

The anion represented by symbol $A^\ominus$ can be derived from any organic or mineral acid, of which the pharmaceutically acceptable acids are preferred. Examples of the applicable acids are as follows: hydrochloric acid, hydrobromic acid, sulfuric acid, phosphoric acid, nitric acid, perhaloic acids (particularly perchloric acid), formic acid, acetic acid, propionic acid, glycolic acid, maleic acid, succinic acid, tartaric acid, citric acid, salicylic acid, benzoic acid, lactic acid, malic acid, mruvic acid, ascorbic acid, phenylacetic acid, anthranilio acid, p-aminobenzoic acid, p-hydroxybenzoic acid, p-amino-salicylic acid, embonic acid, fumaric acid, cinnamic acid, furthermore sulfonic acids, such as methanesulfonic acid, ethanesulfonic acid, halogenated sulfonic acids, toluenesulfonic acids, naphthalenesulfonic acids, sulfanilic acid or cyclohexylsulfaminic acid, as well as amino acids, such as aspartic acid, glutamic acid, N-acetyl-aspartic acid or N-acetylglutamic acid.

The 10-bromo-vincaminic acid esters of formula (I), prepared according to the invention, possess valuable therapeutic properties. These compounds can be applied in the treatment of behavioral disorders originating from senile cerebrovascular damages and sclerosis, furthermore in the therapy of disorientations following cranial injuries.

The German patent specification No. 2,458,164 reports on the preparation of some representatives of the 10-bromo-vincaminic acid esters having formula (I). According to this known method a 3-(1-ethyl-9-halo-octahydroindoloquinolizin-1-yl)-2-methoxy-propenic acid methyl ester is treated with an acid to yield a mixture of the respective 10-halo-vincamines and 10-halo-apovincamines. At the end of the reaction the 10-halo-vincamine should be separated from the by-product in an additional step. The starting substance of the above process is prepared from ethyl-(3-[p-toluenesulfonyloxy]-prop-1-yl)-malonaldehyde acid ester diethylacetal in a five-step synthesis, through complicated intermediates.

The 10-bromo-vincaminic acid esters and their homologues can be prepared according to the process of the invention from new, easily available starting substances in five easily performable reaction steps through simple new intermediates. The process of the invention provides the end-products in high yields and in a pure state, free of the respective apovincaminic acid derivatives.

The compounds of formula (II), used as starting substances in the process variant (a) of the invention, are known and easily accessible materials. The malonate compounds of formula (III), applied as reactants, can be prepared according to the method of E. Fischer and H. Bergmann (Ann. 398, 120 [1913]).

The bromoaniline derivatives of the formula (II) can be diazotized with an alkali nitrite, primarily sodium nitrite, in an aqueous, preferably concentrated aqueous solution of a strong mineral acid, particularly in concentrated aqueous hydrochloric acid, at a temperature of $-10°$ C. to $+5°$ C.

The resulting solution of the diazonium salt of the bromoaniline starting substance is then reacted with a solution of a compound of formula (III) in an inert organic solvent. As the inert organic solvent preferably an aliphatic alcohol, such as dry ethanol, can be applied. The reaction is performed preferably in the presence of an alkaline agent, e.g. an alkali metal hydroxide, such as potassium hydroxide or sodium hydroxide. The alkaline agent is added preferably to the alcoholic solution of the formula (III) compound before introducing it into the acidic solution of the diazonium salt.

The product of the above reaction, i.e. the phenylhydrazone derivative of formula (IV), is obtained in the form of a cis-trans isomeric mixture. It is not necessary to separate the individual isomers from one another at this stage, since in the subsequent cyclization step both isomers are converted into the same compound of formula (V).

The cyclization can be performed in an organic solvent, such as in an aliphatic alcohol (preferably n-butanol), at elevated temperatures, preferably at 40°–180° C., optionally in the presence of a small amount of water.

The compounds of formula (V), obtained as described above, can be converted into 5-bromo-tryptamine derivatives of the formula (VI) in two different ways. According to one of these methods the compounds of formula (V) are subjected first to alkaline hydrolysis, and the resulting 5-halo-tryptamine-2-carboxylic acid (formula (V), R⁴=hydrogen) is decarboxylated by heating it in an acidic medium. The alkaline hydrolysis is performed preferably by heating the ester in a solution, preferably in an aqueous-alcoholic (such as aqueous-ethanolic) solution, of an inorganic base, preferably sodium or potassium hydroxide. When the reaction is conducted at the reflux temperature of the mixture, the hydrolysis terminates within some hours. The subsequent decarboxylation can be performed e.g. by boiling the carboxylic acid in aqueous sulfuric acid.

According to the other method the compounds of formula (V) are hydrolyzed and decarboxylated in a single step in an acidic medium. The reaction is performed in a solution of a strong mineral acid, such as in 10 to 20% aqueous sulfuric acid, by boiling the mixture for several hours.

The 5-halo-tryptamine derivatives of formula (VI), obtained according to one of the above methods, are reacted then with a 2-alkyl-pentanolide of formula (VII) in an organic solvent which does not effect the reaction.

It is preferred to apply an aromatic hydrocarbon, such as xylene, toluene or benzene, as inert organic solvent. The reaction is performed under heating, preferably at the reflux temperature of the mixture, and it terminates within about 2 to 6 hours.

The resulting compound of formula (VIII) can be subjected then to ring closure preferably in the reaction mixture where it was formed. This reaction is performed in the presence of a phosphorus compound which reacts with water and in the optional presence of an elemental halogen or hydrohalic acid. The reaction is conducted under heating, preferably at the reflux temperature of the mixture. At the end of the reaction the mixture is treated with a base under heating.

As phosphorus compounds which react with water there can be used various compounds of phosphorus formed with oxygen and/or a halogen, such as phosphorus pentachloride, phosphorus trichloride, phosphorus oxychloride, etc., furthermore phosphorus pentoxide in the presence of hydrochloric acid or phosphorus trioxide in the presence of bromine. These phosphorus compounds are used in equimolar amounts or, preferably, in an excess over the equimolar value. In this latter instance the excess of the phosphorus compound is removed at the end of the reaction e.g. by boiling the mixture with water or an alcohol.

In the above reaction the intermediate of formula (VIII) is dissolved or suspended in an organic solvent, and reacted with a phosphorus compound as defined above at a temperature of 50° C. to 250° C., preferably at 110° C. to 160° C. As the solvent, a halogenated hydrocarbon, particularly chloroform, carbon tetrachloride, dichloroethane or chlorobenzene can be used. If the phosphorus compound applied in the reaction is liquid, the excess of the phosphorus compound can also serve as a reaction medium.

At the end of the reaction the mixture is treated with a base, e.g. with an alkali metal or alkaline earth metal hydroxide, such as sodium hydroxide, potassium hydroxide or barium hydroxide, or with a basic alkali metal salt, such as sodium carbonate or trisodium phosphate. This treatment can be performed at room temperature or at elevated temperatures, such as about 30° C. to 80° C., or even at the boiling point of the reaction mixture. The base can be introduced as a solid substance or as an aqueous solution or suspension.

According to a preferred method of the invention phosphorus oxychloride is applied as a phosphorus compound in the ring closure reaction, and an excess of this compound serves as a reaction medium. The reaction is performed at the boiling point of the mixture, and then the excess of phosphorus oxychloride is removed in a conventional manner by vacuum distillation. In the above process a halogenated hydrocarbon, such as dichloroethane or chloroform, can also be used as reaction medium beside phosphorus oxychloride; the reaction is performed preferably at the boiling point of the mixture in this latter instance, too.

The acid addition salts of formula (IX) can be converted into the respective free bases by treating them with an alcoholic solution of an inorganic base.

Of the acid addition salts of the compounds having formula (II) the perhalogenates, such as perchlorates and perbromates, are particularly preferred; salts formed with other appropriate mineral or organic acids can be used, however, as well.

In order to liberate the free bases of formula (IX) from their acid addition salts the salts are treated with a strong base in an inert organic solvent. The resulting free base of formula (IX) can be reacted with a compound of formula (X) without separating it from the solution.

It is preferred to apply a dilute aqueous solution of an inorganic base, such as of an alkali metal hydroxide, to liberate the bases of formula (IX) from their acid addition salts. Of the inert organic solvents applicable in this step e.g. halogenated hydrocarbons, such as chloroform, carbon tetrachloride, dichloromethane, 1,2-dichloroethane, trichloroethylene, etc., are to be mentioned; dichloromethane proved to be particularly preferable. The bases of formula (IX) are liberated from their acid addition salts preferably in an inert gas atmosphere, such as in an argon or nitrogen atmosphere. The reaction proceeds within a short time at room temperature.

The organic solution of the free base of formula (IX), liberated from its acid addition salt as described above, is treated then with a compound of formula (X). If desired, an additional inert organic solvent, such as tert.-butanol, can also be introduced into the reaction mixture. When reacting a free base of formula (IX), as liberated from its acid addition salt, with an acrylate of formula (X), the reaction time and temperature have no decisive role; it is preferred, however, to perform the reaction at room temperature for about 6 hours to 6 days. The reaction can be performed in an inert gas atmosphere, such as in an argon or nitrogen atmosphere.

The compounds of formula (XI), utilized as starting substances in the process variant (b) of the invention, can be prepared from the respective tryptamine derivatives by ring closure as described in the Hungarian patent specification No. 167,366.

The compounds of formula (II) are brominated preferably with elemental bromine, but other brominating agents, such as N-bromosuccinimide, can be used as well.

Bromination is performed in the presence of an inert organic solvent or solvent mixture. As solvents e.g. apolar organic liquids, such as halogenated aliphatic hydrocarbons (e.g. chloroform, dichloromethane, etc.), furthermore polar organic liquids, such as organic acids (e.g. glacial acetic acid) can be used. In some instances a small amount of a second solvent, such as an aliphatic alcohol (e.g. methanol) can also be added to the main solvent (for instance, to glacial acetic acid), thereby conducting the reaction in a solvent mixture.

When bromination is performed in an apolar organic solvent, such as in a halogenated aliphatic hydrocarbon, it is preferred to add a Lewis acid to the reaction mixture. As Lewis acid e.g. iron(III)chloride, zinc chloride, aluminium chloride, stannic chloride, boron trifluoride, etc. can be used.

Bromination is performed preferably at room temperature. The reaction proceeds within about 0.5 to 2 hours, preferably within one hour.

The 1-(2'-alkoxycarbonylethyl)-1-alkyl-1,2,3,4,6,7-hexahydro-12H-indolo[2,3-a]quinalizinium salts of formula (II), used as starting substances in process variant (c), can be prepared as described in the Hungarian patent specification No. 171,660 by reacting the appropriate 1-alkyl-hexahydroindoloquinalizinium with acrylic acid esters.

The starting substances of formula (II) are brominated preferably with elemental bromine; however, other known brominating agents leading to the formation of the required 9-bromo compounds, such as N-bromo-succinimide, can also be used with good results.

Bromination is performed in an organic solvent or solvent mixture which does not affect the reaction. For this purpose e.g. apolar organic solvents, such as halogenated aliphatic hydrocarbons, e.g. chloroform an dichloromethane, and polar organic solvents, such as glacial acetic acid, can be used. Small amounts of other organic solvents, such as aliphatic alcohols, e.g. methanol, can also be added to the above solvents, e.g. to glacial acetic acid; these solvent mixtures can also be used to advantage as the reaction media.

When bromination is performed in an apolar organic solvent, such as in a chlorinated hydrocarbon, it is preferred to conduct the reaction in the presence of a Lewis acid, such as ferric chloride, zinc chloride, aluminium chloride, stannic tetrachloride or boron trifluoride.

The reaction is performed preferably at room temperature. The reaction proceeds generally within 0.5 to 4 hours, most frequently within 2 to 3 hours.

The product of processes (a), (b) or (c), which forms initially an intramolecular salt, can be converted into an acid addition salt of formula (XIIIb), wherein $R^2$ and $R^3$ are as defined above and $A^-$ stands for the anion of an acid, by adding an acid to the mixture. It is preferred to apply a mineral acid, such as a hydrohalic acid (e.g. hydrochloric acid) or a perhaloic acid (e.g. perchloric acid) for this purpose.

The red oily intramolecular salt can be treated, however, directly with an aliphatic alcohol of formula $R^5$—OH, such as with methanol, ethanol, n-propanol, isopropanol, n-butanol, etc., to obtain a well crystallizable alkoxy derivative of formula (XIIIa), wherein $R^2$, $R^3$ and $R^5$ are as defined above. This alkoxy compound separates from the alcoholic reaction medium in crystalline state.

The compounds of formula (XIIIa) or (XIIIb) are subjected then to selective reduction. The selective reduction, whereupon the double bond in ring C is saturated without the simultaneous splitting of the halogen atom attached to the aromatic ring, is performed according to methods known per se. It is preferred to use a chemical reducing agent, particularly a complex metal hydride, primarily a borohydride (such as lithium borohydride, sodium borohydride or potassium borohydride) in this step.

The borohydride reduction can be performed in an inert solvent or suspending agent, preferably in an aliphatic alcohol or in an aqueous aliphatic alcohol (such as in methanol or aqueous methanol). The borohydride is added in excess, preferably in a 1.5 to 7 molar excess, to the reaction mixture. Reaction time and temperature have no decisive role and can be varied in accordance with the reactivity of the starting substances applied; the reaction is performed, however, generally at about 0° C. by stirring the mixture at this temperatue for about 15 minutes to 3 hours.

According to a preferred method of the invention a compound of formula (XIIIa) is suspended in an aliphatic alcohol, the suspension is cooled to about 0° C., and at this temperature sodium borohydride is added to the mixture in small portions.

The reaction mixture is processed according to conventional techniques: the excess of the reducing agent is decomposed first by acidifying the mixture, thereafter the mixture is evaporated, the residue is dissolved in water, the solution is rendered alkaline, extracted with an inert organic solvent, and the product is separated from this latter solution by evaporating the solvent.

The processing of the mixture yields the product generally in crystalline state. When the product, consisting of a mixture of the compounds having formulae (XVa) and (XIVb) is obtained as an amorphous powder or in oily form, it can be crystallized easily from an appropriate solvent, such as from an aliphatic alcohol (e.g. methanol, ethanol or isopropanol) or an aliphatic ether (e.g. diethyl ether, etc.).

The product of the selective reduction step is an isomeric mixture consisting of compounds of formulae (XIVa) and (XIVb). These isomeric compounds can be separated from each other according to conventional physical methods, such as by fractional crystallization from an appropriate organic solvent. For this purpose lower aliphatic carboxylates, halogenated lower aliphatic hydrocarbons, lower aliphatic alcohols (such as methanol, ethanol or isopropanol), lower aliphatic ethers or mixtures of these solvents can be used.

The compounds of formulae (XIVa) and (XIVb) can also be separated from each other on the basis of the differences in their physical properties, such as on the basis of their different $R_f$ values. One of these methods is preparative layer chromatography, which utilizes the fact that the $R_f$ value of the trans compound is higher than that of the cis isomer. It is preferred to apply silica gel (such as Merck $PF_{254+366}$ grade silica gel) as adsorbent; various solvent mixtures, such as a 14:2 or 14:3 mixture of benzene and methanol, can be used as eluting agent (see H. Halpaap: Chemie-Ing. Techn. 35, 488 (1963).

The cis and trans isomers of the formulae (XIVa) and (XIVb) can also be separated from each other according to the invention by hydrolyzing first the reaction product obtained in the selective reduction step, and then separating from each other the free acid forms of the isomers by fractional crystallization. According to our experiences the free acid forms of the esters having the formulae (Va) and (Vb) can be separated from each other particularly easily by fractional crystallization. The liberation of the carboxylic acids from their esters is also advantageous with respect to the preparation of the optically active compounds, since the racemic compounds containing a free carboxy group can be resolved very easily through converting them into a diastereomeric salt pair with an optically active base.

The esters of the formulae (XIVa) and (XIVb) can be converted into the corresponding free acids by conventional methods of hydrolysis, such as boiling the esters in an appropriate solvent, e.g. in ethanol, in the presence of an inorganic base, e.g. sodium hydroxide.

The resulting mixture of the racemic or optically active cis- and trans-carboxylic acids can be subjected to fractional crystallization preferably so that the isomeric mixture is dissolved in a hot organic solvent, such as in hot dimethyl formamide, the solution is allowed to cool, the separated crystals of the trans-carboxylic acid with lower melting point are filtered off, and the filtrate is admixed with water in order to precipitate the cis-carboxylic acid with a higher melting point.

The individual racemic or optically active cis- and trans-carboxylic acids, separated from each other as described above, can be converted into their esters by conventional methods. The esters can be prepared e.g. so that the resulting racemic or optically active cis- or trans-carboxylic acids are reacted first with an appropriate halogenating agent, and the acid halides are treated then with an alcohol. In this way a wide variety of racemic or optically active carboxylic acid esters of the formulae (XIVa) or (XIVb) can be prepared.

In the first step of the above esterification process the free carboxylic acids are reacted e.g. with a phosphorus halide, such as phosphorous oxychloride, phosphorous trichloride or phosphorus pentachloride. It is, however, particularly preferred to apply thionyl chloride as halogenating agent in the above step. Halogenation can be performed optionally in an inert organic solvent in the presence of an inorganic or organic base, but if a liquid reactant is applied as halogenating agent, the reaction can also be conducted in the excess of this liquid reactant without adding an inert solvent and a base to the reaction mixture. In the second step of the esterification process the resulting acyl halides are reacted with the appropriate alcohol preferably at the boiling point of the mixture, optionally in the presence of an acid binding agent.

The racemic or optically active free carboxylic acids corresponding to the esters of the formulae (XIVa) and (XIVb) can also be esterified in a single step, by reacting the free acids or their salts with an alkylating agent. Of the salts those formed with alkali metal ions, such as the sodium and potassium salts, are particularly preferred. According to a preferred method alkyl halides, such as alkyl bromides or, more preferably, alkyl iodides, are used as alkylating agents. These alkyl halides may contain straight-chain or branched $C_{1-6}$ alkyl gas preferably primary or secondary alkyl groups, such as methyl, ethyl, n-propyl, isopropyl, n-butyl, sec.-butyl, n-pentyl, isopentyl, n-hexyl or isohexyl groups. Of the alkylating agents the following are particularly preferred: methyl iodide, methyl bromide, ethyl iodide, ethyl bromide, isopropyl bromide, isopropyl iodide, sec.-butyl iodide, sec.-butyl bromide, etc. Alkylation can be performed in a dipolar aprotic solvent, such as in hexamethylphosphoric acid amide or dimethyl formamide. If a free carboxylic acid is used as the starting material in the above process, the reaction is performed in the presence of an inorganic base, such as by adding an aqueous solution of sodium or potassium hydroxide, sodium hydride or, preferably, potassium carbonate to the mixture. Alternatively, the free acid can be reacted first with a base, and the resulting salt can be contacted then with the alkylating agent.

The racemic or optically active 1α-alkyl-1β-alkoxycarbonylethyl-9-bromo-12bαH-octahydroindoloquinolizine compounds of formula (XIVa), obtained as described above, are the starting substances of the next step of the synthesis according to the invention. The isomeric compounds of formula (XIVb) can be oxidized with an alkali bichromate to yield the respective hexahydro compounds of formula (XIIIa) or (XIIIb), which latter can be introduced into the process of the invention as intermediates. Details of this oxidation method are disclosed in our earlier Hungarian patent No. corresponding to the Hungarian patent application No. RI-660.

In the next step of the synthesis according to the invention the compounds of formula (XIVa) are reacted with an alkaline agent, such as with an alkali metal hydride, e.g. sodium hydride or an alkali metal tert.-alkoxide, e.g. lithium, sodium or potassium tert.-butoxide. It is preferred to apply an aromatic hydrocarbon, such as benzene or toluene, as the reaction medium. The resulting compounds of formula (XV) can be converted, if desired, into their acid addition salts by conventional methods.

The compounds of formula (XV) can be nitrosated e.g. with a tertiary alkyl nitrite in an inert solvent, such as in an aromatic hydrocarbon, e.g. benzene or toluene, in the presence of an alkaline agent, preferably of an alkali metal tert.-alkoxide, such as lithium, sodium or potassium tert.-butoxide.

In the next step of the synthesis according to the invention the resulting compounds of formula (XVI) are subjected to deoxyimination. Deoxyimination can be performed by reductive methods, e.g. by treatment with zinc in aqueous acetic acid, by oxidative methods, e.g. by treatment with thallium nitrate, or by a so-called transoximation method, e.g. by treatment with an acid in the presence of a carbonyl compound. This latter method is particularly preferred.

Transoximation is performed preferably so that the compounds of formula (XVI) are dissolved in an organic acid and treated with paraformaldehyde in the presence of an aromatic sulfonic acid. As organic acid e.g. a $C_{1-6}$ alkanecarboxylic acid, such as formic acid, acetic acid, propionic acid, etc., can be applied. Of the aromatic sulfonic acids usable in this reaction p-toluenesulfonic acid is to be mentioned. If desired, the resulting 10-bromo-14,15-dioxo-E-homo-eburnane compounds of formula (XVII) can be converted into their acid addition salts by methods known per se, and/or the racemates can be resolved in a conventional way to yield the pure optically active isomers.

In the last step of the synthesis according to the invention the compounds of formula (XVII) are treated with a base, preferably with an alkali metal tert.-alkoxide, such as lithium, potassium or sodium termt.-butoxide, in the presence of an alcohol of formula $R^1$-OH corresponding to the ester to be prepared. This step yields the required end-products of formula (I).

The reaction mixtures formed in the individual steps of the above synthesis can be processed by conventional methods. Depending on the nature of the compound and of the solvent applied, the intermediates or the end-products can be isolated from the reaction mixtures e.g by filtration or by evaporating the solvent optionally under reduced pressure. If desired, the isolated substances can be purified by recrystallization from an appropriate inert organic solvent. The solvents to be applied for this purpose are selected in accordance with the solubility conditions and crystallization properties of the compounds in question. The reaction mixtures can also be processed by extracting the product from the mixture with an appropriate inert organic solvent, such as dichloromethane, dichloroethane, etc., drying and evaporating the soltuion, and, if necessary, crystallizing the residue from an appropriate solvent. In some instances the product can also be precipitated from the reaction mixture with an appropriate inert organic solvent, such as ether, and isolated by filtration. If desired, the resulting racemic or optically active compounds can be purified further by additional conventional operations, such as by recrystallization.

The products obtained by the process of the invention can also be purified by preparative layer chromatography. For this purpose it is preferred to apply silica gel, such as Merck $PF_{254+366}$ grade silica gel, as adsorbent; various solvent mixtures can be utilized as an eluting agent.

If desired, the racemic or optically active compounds of the formulae (I), (Va), (VI), (VIII), (IX), (XI), (XII), (XIIIa), (XIIIb), (XIVa), (XIVb), (XV), (XVI) or (XVII) obtained according to the method of the invention can be converted into their pharmaceutically acceptable acid addition salts by reacting the free bases with appropriate acids. Examples of the acids applicable for this purposes are mineral acids, such as hydrohalic acid (e.g. hydrochloric acid, hydrobromic acid, etc.), sulfuric acid, phosphoric acid and perhaloic acids (e.g. perchloric acid); furthermore organic carboxylic acids, such as formic acid, acetic acid, propionic acid, oxalic acid, glycolic acid, maleic acid, fumaric acid, succinic acid, tartaric acid, ascorbic acid, citric acid, malic acid, salicylic acid, lactic acid, benzoic acid or cinnamic acid; sulfonic acids, such as methanesulfonic acid, p-toluenesulfonic acid or cyclohexylsulfonic acid; and amino acids, such as aspartic acid, glutamic acid, N-acetyl-aspartic acid, N-acetyl-glutamic acid, etc.

The salt formation is performed preferably in an inert solvent, particularly in an aliphatic alcohol, such as methanol, by dissolving the free base of the formulae (I), (Va), (VI), (VIII), (IX), (XI), (XII), (XIIIa), (XIIIb), (XIVa), (XIVb), (XV), (XVI) or (XVII) in the solvent and acidifying the solution slightly (to about pH=6) with the selected acid. The resulting salt separates from the reaction mixture, or it can be precipitated with an appropriate organic solvent, such as ether.

The compounds of formula (I) contain asymmetric carbon atoms, consequently they can exist in the form of optically active isomers and racemic mixtures. The process of the invention also encompasses the preparation of the optically active antipodes of the end-products. The optically active compounds of formula (I) can be prepared either by resolving the corresponding racemic mixtures in a manner known per se, or by utilizing optically active starting substances. According to a third method, the synthesis is started with a racemic compound of formulae (II), one of the resulting racemic intermediates, such as a compound of the formula (Va), (VI), (VII) or (VIII), is resolved, and the subsequent step(s) of the synthesis is (are) performed on the optically active intermediate(s). If desired, any of the optically active compounds prepared according to the invention can be converted into the respective racemic mixtures by methods known per se.

The compounds of formula (I) can be prepared according to the method of the invention in high yields as easily identifiable pure substances. The analytical data of the products are in good agreement with the calculated ones, and the characteristic IR, NMR and mass spectral peaks of the compounds confirm the assigned structures.

Intermediates of the formulae (IV), (V), (Va), (VI), (VIII), (IX), (XI), (XII), (XIIIa), (XIIIb), (XIVa), (XIVb), (XV), (XVI) and (XVII) are new compounds, not described before in the literature. The new intermediates formed in the process of the invention are biologically active substances and posses valuable pharmacological properties. These new compounds as well as their preparation are also embraced by the scope of the invention.

Pharmacological tests were carried out with the intermediate products of the invention. Particularly the compounds of the formulae (XIVb), (XIIIb), (XIVa) and (IX) turned out to possess considerable pharmacological activity.

Dogs anaesthetized with chloralose-urethane were subjected to blood circulation tests. Arterial blood-pressure, pulse rate, blood circulation in the arteria femoralis and in the arteria carotis interna as well as blood vessel resistance of both blood vessel regions (blood pressure divided by blood circulation) were measured and calculated, resp.

The test compounds were administered intravenously at doses of 1 mg. per kg. of body weight. Each compound was tested in 5 to 6 parallel experiments.

The results are summarized in the following Tables 1 to 4. Abbreviations in the Tables are as follows:
MABP=middle arterial blood pressure
HR=pulse rate
CBF=blood circulation in the arteria carotis interna
CVR=blood vessel resistance in the arteria carotic interna
FBF=blood circulation in the arteria femoralis
FVR=blood vessel resistance in the arteria femoralis

TABLE 1

Effect of 1α-ethyl-1β-(2'-methoxycarbonyl-ethyl)-9-bromo-1,2,3,4,6,7,12,12β-octahydro-indolo[2,3-a]quinolizin on blood circulation
(average ± deviation from the average)

| | Control | Treated |
|---|---|---|
| MABP mmHg, % | 110 ± 5.2 | 84.2 ± 5.5<br>− 23 |
| HR min.⁻¹, % | 187 ± 17 | 204 ± 16<br>+ 9.8 |
| CBF ml. min.⁻¹, % | 90.0 ± 13 | 93.3 ± 13<br>+ 5.7 |
| CVR mmHg min. ml⁻¹, % | 1.4 ± 0.3 | 1.0 ± 0.2<br>− 25 |
| FBF ml. min.⁻¹, % | 31.7 ± 4.8 | 72.5 ± 11<br>+ 138 |
| FVR mmHg min. ml⁻¹, % | 0.89 ± 0.2 | 0.38 ± 0.1<br>− 53 |

TABLE 2

Effect of 1-ethyl-1-(2'-methoxycarbonyl-ethyl)-9-bromo-1,2,3,4,6,7-hexahydro-12H—indolo[2,3-a]quinolizin-5-ium-perchlorate on blood circulation
(average + deviation from the average)

| | Control | Treated |
|---|---|---|
| MABP mmHg % | 144 ± 8.3 | 103 ± 8.6<br>− 27 |
| HR min.⁻¹, % | 153 ± 20.0 | 140 ± 18.0<br>− 8.5 |
| CBF ml. min.⁻¹, % | 56.0 ± 11.0 | 44.8 ± 6.5<br>− 20 |
| CVR mmHg min. ml⁻¹, % | 2.8 ± 0.4 | 2.5 ± 0.3<br>− 13 |
| FBF ml. min.⁻¹, % | 36.8 ± 10.0 | 71.2 ± 18.0<br>+ 110 |
| FVR mmHg min. ml⁻¹, % | 5.7 ± 2.0 | 1.9 ± 0.6<br>− 67 |

TABLE 3

Effect of 1α-ethyl-1β-(2'-methoxycarbonyl-ethyl)-9-bromo-1,2,3,4,6,7,12,12α-octahydro-indolo[2,3-a]quinolizine-D—dibenzoyl-tartarate on blood circulation
(average ± deviation from the average)

| | Control | Treated |
|---|---|---|
| MABP mmHg, % | 145 ± 7.1 | 131 ± 6.2<br>− 9.5 |
| HR min.⁻¹, % | 148 ± 21.0 | 149 ± 20.0<br>0 |
| CBF ml. min.⁻¹ % | 60.6 ± 13.0 | 66.8 ± 12.0<br>+ 12 |
| CVR mmHg min. ml.⁻¹, % | 2.6 ± 0.3 | 2.2 ± 0.3<br>− 18 |
| FBF ml. min.⁻¹ % | 33.0 ± 7.2 | 61.6 ± 13.0<br>+ 94 |
| FVR mmHg min. ml⁻¹ | 5.3 ± 1.2 | 2.5 ± 0.5 |

TABLE 3-continued

Effect of 1α-ethyl-1β-(2'-methoxycarbonyl-ethyl)-9-bromo-
-1,2,3,4,6,7,12,12α-octahydro-indolo[2,3-a]quinolizine-
D—dibenzoyl-tartarate on blood circulation
(average ± deviation from the average)

|  | Control | Treated |
|---|---|---|
| % |  | − 52 |

TABLE 4

Effect of 1-ethyl-9-bromo-1,2,3,4,6,7-hexahydro-12H-in-
dolo[2,3-a]quinolizin-5-ium-perchlorate on blood circulation
(average ± deviation from the average)

|  | Control | Treated |
|---|---|---|
| MABP mmHg | 143 ± 6.4 | 137 ± 5.6 |
| % |  | − 4.2 |
| HR min.$^{-1}$ | 159 ± 22.0 | 148 ± 18.0 |
| % |  | − 7.1 |
| CBF ml. min.$^{-1}$ | 62.8 ± 15.0 | 62.4 ± 15.0 |
| % |  | 0 |
| CVR mmHg min. ml.$^{-1}$ | 2.8 ± 0.6 | 2.8 ± 0.7 |
| % |  | 0 |
| FBF ml. min.$^{-1}$ | 37.6 ± 9.7 | 47.4 ± 14.0 |
| % |  | + 26 |
| FVR mmHg min. ml.$^{-1}$ | 5.3 ± 1.7 | 4.9 ± 2.2 |
| % |  | − 7.5 |

The data of the above Tables show that the new compounds administered intravenously to anaesthetized dogs at a dose of 1 mg. per kg. of body weight induce only low decrease in blood pressure and the pulse rate is almost unchanged. An outstanding activity of the compounds is shown by the decrease of the blood vessel resistance in the extremities (vasodilating activity). The activity is particularly significant in the case of those compounds in Tables 1, 2 and 3 which show a vasodilating activity of 50 to 70%. The blood circulation is simultaneously increased by 90 to 140%. A moderate vasodilation (10 to 25%) was induced by these compounds in the carotic artery region as well.

For comparison purposes, the results of blood circulation tests carried out with vincamine are given in the following Table 5.

TABLE 5

Effect of vincamine on blood circulation
(average ± deviation from the average)

|  | Control | Treated |
|---|---|---|
| MABP mmHg % | 131.2 | 111.8 |
|  |  | −14.7 ± 1.8 |
| HR min$^{-1}$ % | 181.2 | 164.8 |
|  |  | −9.1 ± 2.6 |
| CBF ml. min$^{-1}$ % | 39.2 | 40.8 |
|  |  | +4.1 ± 0.8 |
| CVR mmHg. min. ml$^{-1}$ % | 3.25 | 2.94 |
|  |  | −9.5 ± 2.4 |
| FBF ml. min$^{-1}$ % | 35.9 | 42.78 |
|  |  | +19.2 ± 3.5 |
| FVR mmHg. min. ml$^{-1}$ % | 3.65 | 2.61 |
|  |  | −28.5 ± 5.4 |

The invention also encompasses the methods in which one of the above intermediates is applied as starting substance and only the remaining steps of the synthesis are carried out; or in which the synthesis is terminated at any of the above intermediates.

It is to be mentioned that the intermediates formed in the process of the invention should not be isolated necessarily, but the next step of the synthesis can be performed directly on the mixtures containing the intermediates in question. This latter method is also embraced by the scope of the invention.

The invention is elucidated in detail by the aid of the following non-limiting Examples.

EXAMPLE 1

Ethyl-5-bromo-tryptamine-2-carboxylate hydrochloride 23.70 g. (0.10 mmoles) of diethyl-3-chloropropylmalonate are dissolved in 70 ml. of abs. ethanol, and a solution of 6.40 g. (0.11 mmoles) of potassium hydroxide in 70 ml. of abs. ethanol is added dropwise to the mixture under stirring and exclusion of atmospheric moisture. The mixture is stirred for a further 2 hours, then it is cooled to −5° C., and a diazonium salt solution, precooled to −5° C., is added to the mixture. The diazonium salt solution is prepared as follows:

17.20 g. (0.10 mmoles) of p-bromoaniline are dissolved in a mixture of 100 ml. of water and 27 ml. of concentrated aqueous hydrochloric acid. The solution is cooled to 0°–3° C., and a solution of 7.00 g. (0.11 mmoles) of sodium nitrite in 15 ml. of water is added dropwise. When diazotization terminates, the pH of the solution is adjusted to 6 by introducing about 77 ml. of 10% aqueous sodium carbonate solution, and the resulting solution is cooled to −5° C.

After introducing the diazonium salt solution the pH of the mixture is adjusted to 7.4 to 7.5 with about 15 ml. of 10% aqueous sodium carbonate solution, and the mixture is stirred for one hour at 0° C. under a nitrogen atmosphere. Thereafter the mixture is acidified to pH=6 with acetic acid, and allowed to stand at room temperature overnight. The separated deep red oil is extracted with dichloromethane. The organic phase is washed first with 2 n aqueous sodium hydroxide solution and then thrice with water, dried over anhydrous magnesium sulfate, filtered, and the filtrate is evaporated to dryness in vacuo. The oily residue, which is a cis-trans isomeric mixture of 2-oxo-5-chloro-valeric acid ethyl ester p-bromo-phenylhydrazone, is separated into the individual isomers by preparative layer chromatography (adsorbent: Silicagel Merck $PF_{254+366}$; eluting agent: a 14:2 mixture of benzene and methanol). $R_f$=0.85 (isomer A) and 0.77 (isomer B).

IR spectrum (in KBr pellets):
Isomer A: 3250 (NH), 1738 (—$COOC_2H_5$), 1680 (C=N), 1605 (aromatic) $cm^{-1}$.
Isomer B: 3300 (NH), 1735 (—$COOC_2H_5$), 1700 (C=N), 1608 (aromatic) $cm^{-1}$.

The oily substance obtained as described above is dissolved in 160 ml. of n-butanol. Some drops of water are added, and the mixture is refluxed under a nitrogen atmosphere for 24 hours. Thereafter the solution is cooled to 0° C., the precipitated ethyl 5-bromo-tryptamine-2-carboxylate hydrochloride is filtered off, washed with a small amount of n-butanol, and dried. 12.50 g. (34.8%) of the above compound are obtained; m.p.: 248°–249° C. (after recrystallization from ethanol).

IR spectrum (in KBr pellets): 3340 (NH), 1705 (ester CO) $cm^{-1}$.

Mass spectrum, m/c %: 312 ($M^+$, 19.6), 283 (100), 237 (54.5), 208 (25.6), 127 (34), 101 (13.1).

$^1$H-NMR spectrum (in $CDCl_3$):δ=7.82–7.28 (3H, m, aromatic protons), 4.44 (2H, ester, —$\underline{CH_2}$—$CH_3$), 1.42 (3H, t, ester, —$CH_2$—$CH_3$).

EXAMPLE 2

5-Bromo-tryptamine-2-carboxylic acid 1.00 g. (2.87 mmoles) of ethyl-5-bromo-tryptamine-2-carboxylate hydrochloride are boiled for 2 hours in a mixture of 10 ml. of ethanol and 10 ml. of 4 n aqueous sodium hydroxide solution. The mixture is cooled with ice, acidified to pH 6 with glacial acetic acid, and the separated crystals are collected by filtration. 0.75 g. (91%) of 5-bromo-tryptamine-2-carboxylic acid are obtained; m.p.; 248°–249° C.

IR spectrum (in KBr pellets): 3320 (NH), 1585 ($COO^-$) $cm^{-1}$.

Analysis: Calculated for $C_{11}H_{11}N_2O_2Br$ (M.wt.: 283.13): C: 46.63%, H: 3.91%, N: 9.98%. Found: C: 46.52 %, H: 3.85 %, N: 9.92%.

EXAMPLE 3

5-Bromo-tryptamine

A mixture of 1.00 g. (3.53 mmoles) of 5-bromo-tryptamine-2-carboxylic acid and 80 ml. of 10% aqueous sulfuric acid is stirred and refluxed for 30 hours. The pH of the mixture is adjusted to 9 with concentrated aqueous ammonia under cooling in an ice bath, and the alkaline mixture is extracted with 4×20 ml. of chloroform. The organic extracts are combined, washed with 5% aqueous sodium hydroxide solution and then with water, dried over anhydrous magnesium sulfate, filtered, and the filtrate is evaporated in vacuo. 0.48 g. (58%) of 5-bromo-tryptamine are obtained as an oily residue.

A part of the oily residue is dissolved in ethanol and converted into the formate by introducing formic acid. The formate salt melts at 175°–176° C. after recrystallization from ethanol.

Analysis: Calculated for $C_{11}H_{12}N_2O_2Br$ (M.wt.: 284.14): N: 9.86%. Found: N: 9.71%.

EXAMPLE 4

1Ethyl-9bromo-1,2,3,4,6,7-hexahydro-12H-indolo-[2,3-a]quinolizin-5-ium perchlorate 0.48 g. (2.0 mmoles) of 5-bromo-tryptamine and 0.30 g. (2.3 mmoles) of 2-ethyl-pentanolide are dissolved in 5 ml. of abs. xylene, and the solution is refluxed for 4 hours. The reaction mixture is evaporated in vacuo, the residue is triturated twice with 3 ml. each of petroleum ether, thereafter it is dried in a desiccator. 0.59 g. (80%) of N-(α-ethyl-δ-hydroxyl-valeroyl)-5-bromo-tryptamine are obtained.

IR spectrum (in KBr pellets): 3320 (NH, OH, broad), 1640 (acid amide CO) $cm-1$.

The resulting 0.59 g of N-(α-ethyl-δ-hydroxy-valeroyl)-5-bromo-tryptamine are admixed, without purification, with 5 ml. of phosphorous oxychloride. The mixture is refluxed for 6 hours, thereafter the excess of phosphorous oxychloride is distilled off in vacuo, the residue is admixed with 5 ml. of 4 n aqueous sodium hydroxide solution under cooling with ice, and the mixture is stirred at room temperature for 15 minutes. The organic phase is separated and the aqueous phase is extracted thrice with 3 ml. each or dichloroethane. The organic solutions are combined, dried over anhydrous magnesium sulfate, and filtered. The solvent is removed from the filtrate by vacuum distillation, the oily residue (0.65 g.) is dissolved in 3 ml. of methanol, and the pH of the solution is adjusted to 6 by introducing a 70 % aqueous perchloric acid solution. The precipitated crystals are collected by filtration, washed with cold methanol and dried. 0.40 g. (46%, calculated for 5-bromo-tryptamine) of 1-ethyl-9-bromo-1,2,3,4,6,7-hexahydro-12H-indolo[2,3-a]quinolizin-5-ium perchlorate are obtained; m.p.: 233°–234° C. (after recrystallization from methanol).

IR spectrum (in KBr pellets): 3250 (indole NH), 1622, 1545 (C=N) $cm^{-1}$.

Analysis: Calculated for $C_{17}H_{20}N_2ClBrO_4$ (M.wt.: 431.72): C: 47.29%, H: 4.67%, N: 6.49%. Found: C: 47.08%, H: 4.55%, N: 6.36%.

EXAMPLE 5

1-Ethyl-1-(2′-methoxycarbonylethyl)-9-bromo-1,2,3,4,6,7-hexahydro-7aH-indolo[2,3a]quinolizin-5-ium-methoxide 7.00 g. (16.2 mmoles) of 1-ethyl-9-bromo-1,2,3,4,6,7-hexahydro-12H-indolo[2,3-a]quinolizin-5-ium perchlorate are dissolved in 160 ml. of dichloromethane, the solution is poured into a separatory funnel, and the mixture of 28 ml. of a 10% aqueous sodium hydroxide solution and 111 ml. of water is added. The two-phase mixture is shaken thoroughly, the organic phase is separated, dried over anhydrous potassium carbonate, and filtered. 8.90 g. (103.5 mmoles) of methyl acrylate are added to the filtrate, which is a dichloro-methane solution of the free base. The resulting mixture is allowed to stand at room temperature for 2 days, thereafter the solvent is evaporated in vacuo, and the oily residue is crystallized from methanol. In this way 4.70 g. (64.5%) of 1-ethyl-1-(2′-methoxycarbonylethyl)-9-bromo-1,2,3,4,6,7-hexahydro-7aH-indolo[2,3-a]quinolizin-5-ium methoxide are obtained in the form of orange red crystals; m.p.: 140°–142° C. (from methanol).

IR (in KBr pellets): 1730 (—$COOCH_3$), 1560, 1480 (C=H) $cm^{-1}$.

Mass spectrum: m/e (%)=420 (8.5), 419 (9.3), 418 ($M^+$, 11), 417 (8.8), 405 (0.8), 403 (1.1), 401 (0.6), 389 (1.7), 387 (2.5), 385 (2.9), 383 (1.9), 347 (9.9), 345 (13), 332 (43), 317 (99), 315 (100), 303 (11), 301 (12), 250 (5.8), 249 (6.0), 248 (6.0), 247 (5.5).

Under the conditions of the mass spectral analysis methanol and a bromine-containing compound (molecular weight: 418) can also be detected in the vapor phase of the sample.

$^1$H-NMR ($CDCl_3$): δ=7.47–7.05 (3H, m, aromatic protons), 3.55 (6H, s —$COOCH_3$, —$OCH_3$), 0.82 (3H, t, —$CH_2\underline{CH}_3$) ppm.

0.1 g. of the above product are suspended in 1 ml. of methanol, and the pH of the suspension is adjusted to 6 with 70% aqueous perchloric acid solution. The separated crystals are collected by filtration, washed with a small amount of methanol and dried. 0.095 g. of 1-ethyl-1-(2′-methoxycarbonylethyl)-9-bromo-1,2,3,4,6,7-hexahydro-12H-indolo[2,3-a]quinolizin-5-ium perchlorate are obtained; m.p.: 221°–222° C. (after recrystallization from methanol).

IR (in KBr pellets): 3300 (indole NH), 1718 (—$COOCH_3$), 1620 and 1538 (C=N) $cm^{-1}$.

EXAMPLE 6

1-Ethyl-9-bromo-1,2,3,4,6,7-hexahydro-12H-indolo[2,3a]quinolizin-5-ium perchlorate 48 ml. of a 10% aqueous sodium hydroxide solution and 192 ml. of water are added to a solution of 12.00 g. (34 mmoles) of 1-ethyl-1,2,3,4,6,7-hexahydro-12H-indolo[2,3-a]quinolizin-5-ium perchlorate in 276 ml. of dichloromethane, and the mixture (pH=11) is well shaken in a separatory funnel. The organic phase is separated, dried over solid potassium carbonate, filtered, and the filtrate is evaporated to dryness in vacuo. The residue is dissolved in methanol, the solution is acidified to pH 6 with methanolic hydrochloric acid, and the solvent is distilled off in vacuo. The oily residue is dissolved in 70 ml. of glacial acetic acid, 5 ml. of methanol are added, and a solution of 6.55 g. (41 mmoles) of bromine in 30 ml. of glacial acetic acid is introduced into the mixture at room temperature under constant stirring. After about one hour the product separates as an oil onto the wall of the flask. Glacial acetic acid is decanted, the oily residue is dissolved in 30 ml. of warm methanol, and 2.92 ml. of 70% aqueous perchloric acid are added to the solution. The pH of the mixture is thus adjusted to 5. The separated product is filtered off, washed with a small amount of cold methanol and dried. 9.02 g. of 1-ethyl-9-bromo-1,2,3,4,6,7-hexahydro-12H-indolo[2,3-a]quinolisin-5-ium perchlorate are obtained.

The glacial acetic acid solution decanted from the product in the above step is evaporated in vacuo, the residue is dissolved in 10 ml. of warm methanol, and the solution is acidified to pH 5 with 70% aqueous perchloric acid solution. The separated product is filtered off, washed with cold methanol and dried. In this way further 1.47 g. of the above product are obtained; thus the total yield is 10.49 g. (71.4%). The product melts at 233°–234° C.

IR (in KBr): 3250 (indole NH), 1622, 1545 (C=N) $cm^{-1}$.

Analysis: Calculated for $C_{17}H_{20}N_2ClBrO_4$ (M.wt.: 431.72): C: 47.29%, H: 4.67%, N: 6.49%. Found: C: 47.08%, H: 4.55%, N: 6.36%.

EXAMPLE 7

1-Ethyl-1-(2′-methoxycarbonylethyl)-9-bromo-1,2,3,4,6,7-hexahydro-12H-indolo[2,3-a]quinolizin-5-ium methoxide 4.39 g. (10 mmoles) of 1-ethyl-1-(2′-methoxycarbonylethyl)-1,2,3,4,6,7-hexahydro-12H-indolo[2,3-a]quinolizin-5-ium perchlorate are shaken with a mixture of 5 ml. of 10% aqueous ammonia and 50 ml. of dichloromethane. The phases are separated, the organic phase is dried over 10 g. of solid anhydrous sodium sulfate, filtered, the filtrate is evaporated to a final volume of about 40 ml., and 0.1 g. of dry ferric chloride are added to this concentrate. 2.08 g. (0.67 ml., 13 mmoles) of elemental bromine are added dropwise, under vigorous stirring, to this mixture at 25° C. The addition takes place in 5 minutes. The reaction mixture is stirred at room temperature for 2 hours, thereafter it is rendered alkaline with 10 ml. of 10% aqueous ammonia, and the precipitated ferric hydroxide is filtered off. The organic phase of the filtrate is separated, dried over 10 g. of solid anhydrous sodium sulfate, filtered, and the filtrate is evaporated. The oily residue is admixed with 10 ml. of methanol, whereupon the product separates in crystalline form containing lattice-bound methanol. In this way 3.81 g. (85%) of 1-ethyl-1-(2′-methoxycarbonylethyl)-9-1,2,3,4,6,7-hexahydro-12H-indolo[2,3-a]quinolisin-5-ium methoxide are obtained; m.p.: 140°–142° C.

$^1$H-NMR (in $CDCl_3$):=0.8 (t, 3H, —$CH_2CH_3$), 7.6 (2H, Ar 10–11H), 8.1 (1H, Ar 8H) ppm.

EXAMPLE 8

1-Ethyl-1-(2′-methoxycarbonylethyl)-9bromo-1,2,3,4,6,7-hexahdryo-12H-indolo[2,3-a]quinolizin-5-ium methoxide 4.39 g. (10 mmoles) of 1-ethyl-1-(2′-methoxycarbonylethyl)-1,2,3,4,6,7-hexahydro-12H-indolo[2,3-a]quinolizin-5-ium perchlorate are shaken with a mixture of 5 ml of 10% aqueous ammonia and 50 ml. of dichloromethane. The phases are separated, the organic phase is dried over 10 g. of solid anhydrous sodium sulfate, and then filtered. 0.5 g. of dry gaseous hydrochloric acid are introduced into the filtrate, thereafter 50 ml of glacial acetic acid are added, and dichloromethane, is distilled off in vacuo. 0.67 ml. (2.08 g., 13 mmoles) of elemental bromine are added dropwise, under vigorous stirring, to the residue at 25° C. The reaction mixture is stirred at room temperature for 3 hours, the separated product is filtered off, and suctioned well to remove the residue of acetic acid. The still wet product is suspended in 40 ml. of dichloromethane, the dilute suspension is rendered alkaline with 14 ml. of 10% aqueous ammonia, and the phases are separated from each other. The organic phase is dried over 10 g. of solid anhydrous sodium sulfate, filtered off, and the filtrate is evaporated. The obtained oily residue is triturated with 10 ml. of methanol, whereupon the product separates in crystalline form containing lattice-bound methanol. In this way 3.15 g. (70%) of 1-ethyl-1-(2′-methoxycarbonylethyl)-9-bromo-1,2,3,4,6,7-hexahydro-12H-indolo[2,3-a]quinolizin-5-ium methoxide are obtained; m.p.: 140°–142° C. The NMR spectrum of the product is identical with that given in Example 7.

EXAMPLE 9

1-Ethyl-1-(2′-methoxycarbonylethyl)-9-bromo-1,2,3,4,6,7-hexahydro-12H-indolo[2,3-a]quinolizin-5-ium hydrobromide 4.39 g. (10 mmoles) of 1-ethyl-1-(2′-methoxycarbonylethyl)-1,2,3,4,6,7-hexahydro-12H-indolo[2,3-a]quinolizin-5-ium perchlorate are shaken with a mixture of 5 ml. of 10% aqueous ammonia and 50 ml. of dichloromethane. The phases are separated, the organic phase is dried over 10 g. of solid anhydrous sodium sulfate and filtered. The filtrate is admixed with 50 ml. of glacial acetic acid, and dichloromethane is distilled off in vacuo. 0.67 ml. (13 mmoles, 2.08 g.) of elemental bromine are added dropwise, under vigorous stirring, to the residue at 25° C. The reaction mixture is stirred at room temperature for 3 hours, the precipitated yellow, crystalline product is filtered off and dried. In this way 4.5 g. of 1-ethyl-1-(2′-methoxycarbonylethyl)-9-bromo-1,2,3,4,6,7-hexahydro-12H-indolo[2,3-a]quinolizin-5-ium hydrobromide are obtained; yield: 90%, m.p.: 127°–128° C. The NMR spectrum of the product has the characteristic bands as indicated in Example 7.

EXAMPLE 10

1-Ethyl-1-(2′-methoxycarbonylethyl)-9-bromo-1,2,3,4,6,7-hexahydro-12H-indolo[2,3-a]quinolizin-5-ium perchlorate 0.1 g. of 1-ethyl-1-(2′-methoxycarbonylethyl)-9-bromo-1,2,3,4,6,7-hexahydro-12H-indolo[2,3-a]quinolizin-5-ium methoxide (prepared as described in Example 7) are suspended in 1 ml. of methanol, and the pH of the suspension is adjusted to 6 by introducing a 70% aqueous perchloric acid solution. The separated crystalline product is filtered off, washed with a small amount of methanol and dried. In this way 0.095 g. of 1-ethyl-1-(2'-methoxycarbonylethyl)-9-bromo-1,2,3,4,6,7-hexahydro-12H-indolo[2,3-a]quinolisin-5-ium perchlorate are obtained; m.p.: 221°–222° C. (after recrystallization from methanol).

IR spectrum (in KBr): characteristic bands at 3300 (indole —NH), 1718 (—COOCH$_3$), 1620 and 1538 (C=N) cm$^{-1}$.

EXAMPLE 11

(±)-1α-Ethyl-1β-(2'-methoxycarbonylethyl)-9-bromo-1,2,3,4,6,7,12,12bα-octahydroindolo[2,3-a]quinolizin and (±)-1α-ethyl-1β-(2'-methoxycarbonylethyl)-9-bromo-1,2,3,4,6,7,12,12bβ-octahydroindolo[2,3-a]quinolizin 6.50 g. (14.4 mmoles) of 1-ethyl-1-(2'-methoxycarbonylethyl)-9-bromo-1,2,3,4,6,7-hexahydro-7aH-indolo[2,3-a]quinolizin-5-ium methoxide are dissolved in 20 ml. of a 1:1 mixture of dichloromethane and methanol, and 0.55 g. of sodium borohydride are added to the solution in small portions at 0° C. under stirring. After the addition the mixture is stirred for an additional 30 minutes, then it is acidified with acetic acid to pH=6, and evaporated to dryness in vacuo. The pH of the residue is adjusted to 8 to 9 with 5% aqueous sodium carbonate solution, and the resulting solution is extracted with dichloromethane. The organic phase is separated, dried over anhydrous magnesium sulfate, filtered, and the filtrate is evaporated in vacuo. The oily residue, weighing 6.10 g., is subjected to preparative thin layer chromatography (adsorbent: silica gel Merck KG-PF$_{254+366}$; solvent: a 14:3 mixture of benzene and methanol) in order to separate the isomers from each other. Separation is performed on the basis that the R$_f$ value of the 12bβ isomer is higher than that of the 12bα derivative. By eluting with a 10:1 mixture of dichloromethane and methanol 2.70 g. (44.5%) of (±)-1α-ethyl-1β-(2'-methoxycarbonylethyl)-9-bromo-1,2,3,4,6,7,12,12bα-octahydroindolo[2,3-a]quinolizine are isolated; m.p.: 166°–168° C. (after recrystallization from methanol).

IR (in KBr pellets): 3380 (indole NH), 2800, 2750 (Bohlmann bands), 1720 (—COOCH$_3$) cm$^{-1}$.

Mass spectrum: m/e (%)=420 (81.6), 418 (M+, 812), 405 (8.1), 403 (8.1), 389 (9.5), 387 (5.4), 347 (95.5), 345 (100), 317 (2.6), 315 (2.6), 277 (28.9), 275 (30.7), 250 (27.9), 248 (31.6), 168 (19.5).

$^1$H-NMR (DMSO-d$_6$, CDCl$_3$): δ=7.62–7.12 (3H, m, aromatic protons), 3.58 (3H, s, —COOCH$_3$), 3.50 (1H, s, 12bH), 1.11 (3H, t, —CH$_2$CH$_3$) ppm.

0.1 g. of the above 12bα derivative are suspended in 1 ml. of methanol, and the pH of the suspension is adjusted to 6 with methanolic hydrochloric acid. The separated crystals are collected by filtration, washed with a small amount of methanol and dried. 0.095 g. of (±)-1α-ethyl-1β-(2'-methoxycarbonylethyl)-9-bromo-1,2,3,4,6,7,12,12-bα-octahydroindolo[2,3-a]quinolizin-5-ium hydrochloride are obtained; m.p.: 223°–225° C.

In an analogous manner 2.02 g. (33.3%) of (±)-1α-ethyl-1β-(2'-methoxycarbonylethyl)-9-bromo-1,2,3,4,6,7,12,12bβ-octahydroindolo[2,3-a]quinolizin are separated from the thin layer chromatographical fraction with higher R$_f$ value. After recrystallization from methanol the compound melts at 140°–142° C.

IR (in KBr pellets): 330 (indole NH), 2830, 2750 (Bohlmann bands), 1710 (—COOCH$_3$) cm$^{-1}$.

Mass spectrum: m/e (%)=420 (100), 418 (M$^{30}$, 100), 405 (11.2), 403 (11.9), 389 (11.1), 387 (9.9), 347 (90.2), 345 (90.8), 317 (8.3), 315 (7.4), 277 (26.5), 275 (27.5), 250 (25.6), 248 (27.1), 168 (15).

$^1$H-NMR (CDCl$_3$): δ=9.00 (1H, s, indole proton), 7.62–7.10 (3H, m, aromatic protons), 3.80 (3H, s, —COOCH$_3$), 3.33 (1H, s, 12bH), 0.68 (3H, t, —CH$_2$CH$_3$) ppm.

EXAMPLE 12

(±)-1α-Ethyl-1β-(2'-methoxycarbonylethyl)-9-bromo-1,2,3,4,6,7,12,12bα-octahydroindolo[2,3-a]quinolizine 1.1 g. (2.63 mmoles) of the isomeric mixture obtained as described in Example 11 are dissolved in a warm mixture of 5 ml. of ethanol and 0.3 ml. of water. 0.35 g. of solid sodium hydroxide are added to the solution, and the mixture is refluxed for one hour. Thereafter the solvent is evaporated in vacuo, the residue is dissolved in 13 ml. of water, and the pH of the solution is adjusted to 6 with 10% aqueous acetic acid. The separated substance, consisting of a mixture of the isomeric carboxylic acids, is collected by filtration, washed with water, dried, and recrystallized from 10 ml. of abs. dimethyl formamide. 0.35 g. (33%) of (±)-1α-ethyl-1β-(2'-carboxyethyl)-9-bromo-1,2,3,4,6,7,12,12bα-octahydroindolo[2,3-a]quinolizine are obtained; m.p.: 214°–215° C. IR (in KBr pellets): 3420, 3100 (OH, NH), 1680 (acid CO) cm$^{-1}$.

The resulting 0.35 g. of the 12α isomer are suspended in 10 ml. of dichloromethane, and an excess of diazomethane, dissolved in dichloromethane, is added to the suspension. The solution obtained at the end of the reaction is evaporated to dryness and the residue is crystallized from methanol. 0.3 g. (±)-1α-ethyl-1β-(2'-methoxycarbonylethyl)-9-bromo-1,2,3,4,6,7,12,12bα-octahydroindolo[2,3-a]quinolizine are obtained; m.p.: 166°–168° C. (from methanol). The physical constants of this compound are identical with those of the 12bα isomer obtained according to Example 11.

EXAMPLE 13

(±)-10-Bromo-14-oxo-E-homo-eburnane-(3αH,-17αC$_2$H$_5$)

0.40 g. (0.94 mmoles) of (±)-1α-ethyl-1β-(2'-methoxycarbonylethyl)-9-bromo-1,2,3,4,6,7,12,12bα-octahydroindolo[2,3-a]quinolizine are suspended in 10 ml. of abs. toluene, and 0.27 g. (282 mmoles) of sodium tert.-butoxide are added to the suspension at room temperature with stirring under a nitrogen atmosphere. The mixture is stirred for an additional 3 hours, thereafter the mixture is decomposed by introducing a solution of 0.4 g. of ammonium chloride in 10 ml. of water. The toluene phase is separated, and the aqueous phase is extracted thrice with 6 ml. each of dichloromethane. The organic phases are combined, dried over anhydrous magnesium sulfate, filtered, and the filtrate is evaporated in vacuo. The oily residue is crystallized from methanol. 262 mg. (71.0%) of (±)-10-bromo-14-oxo-E-homo-eburnane-(3αH, 17αC$_2$H$_5$) are obtained; m.p.: 190° C. (from methanol).

IR (in KBr pellets): 2830, 2700 (Bohlmann bands), 1710 (lactam CO) cm$^{-1}$.

Mass spectrum: m/e (%)=386 (M+, 100), 385 (51), 358 (6.4), 357 (9.5), 344 (3.6), 343 (4.1), 330 (13), 329

(10), 315 (5.5), 308 (4.5), 307 (5.5), 306 (2.7), 261 (5.0), 248 (5.9).

$^1$H-NMR (CDCl$_3$+DMSO-d$_6$): δ=8.25 (1H, dd, 12-H), 7.60-7.20 (2H, m, aromatic protons), 4.15 (1H, s, 3-H), 0.86 (3H, t, —CH$_2$CH$_3$) ppm.

EXAMPLE 14

(±)-10-Bromo-14-oxo-15-hydroxyimino-E-homo-eburnane-(3αH.17αC$_2$H$_5$)

0.10 g. (0.25 mmoles) of (±)-10-bromo-14-oxo-E-homo-eburnane-(3αH,17αC$_2$H$_5$) are dissolved in 1 ml. of abs. toluene, and 0.24 ml. of freshly distilled tert.-butyl nitrite are added to the stirred solution at room temperature under a nitrogen atmosphere. After some minutes a suspension of 0.075 g. (0.67 mmoles) of potassium tert.-butoxide in 1 ml. of abs. toluene is introduced into the mixture, the mixture is stirred for an additional 0.5 hours, and then it is decomposed by introducing a solution of 0.2 g. of ammonium chloride in 4 ml. of water. The organic phase is separated, and the aqueous phase is extracted thrice with 2 ml. each of dichloromethane. The organic solutions are combined, dried over anhydrous magnesium sulfate, filtered, and the filtrate is evaporated in vacuo. The oily residue is acidified with methanolic hydrochloric acid to pH=6. In this way 55 ml. (47.0%) of (±)-10-bromo-14-oxo-15-hydroxyimino-E-homo-eburnane-(3αH,17αC$_2$H$_5$) hydrochloride are obtained; m.p.: 247° C. (decomposition).

IR (in KBr pellets): 3400 (OH), 1720 (lactam CO), 1630 (C=N) cm$^{-1}$.

Mass spectrum: m/e (%)=415 (M$^+$, 50), 414 (25), 398 (30), 385 (100), 370 (30), 356 (10), 341 (15), 329 (20), 315 (15), 247 (15), 168 (12), 167 (10), 154 (10), 141 (20).

EXAMPLE 15

(±)-10-bromo-vincamine 0.12 g. (0.26 mmoles) of (±)-10-bromo-14-oxo-15-hydroxyimino-E-homo-eburnane-(3αH,17αC$_2$H$_5$) are dissolved in 2.4 ml. of glacial acetic acid, and 0.24 g. of dry p-toluene sulfonic acid and 0.36 g. of paraformaldehyde are added to the solution. The mixture is maintained at 110° C. for 3.5 hours under exclusion of atomspheric moisture, thereafter it is poured onto ice, and the pH of the mixture is adjusted to 9 with concentrated aqueous ammonium hydroxide. The separated (±)-cis-10-bromo-14,15-dioxo-E-homo-eburnane-(3αH,-17αC$_2$H$_5$) is filtered off, washed with water, and dried in a desiccator over phosphorus pentoxide. 84 mg. of (±)-cis-10-bromo-14,15-dioxo-E-homo-eburnane-(3αH,17αC$_2$H$_5$) are obtained; m.p.: 184° C. (decomposition).

IR (in KBr pellets): 1720 (=C=O), 1690 (amide CO) cm$^{-1}$.

This product is dissolved, without any further purification, in 4 ml. of dichloromethane, the solution is filtered, and the filtrate is evaporated in vacuo. A solution of 0.10 g. of potassium tert.-butoxide in 0.4 ml of abs. methanol is added to the residue, the resulting mixture is warmed to 40° C., and then it is allowed to stand at room temperature for 2 hours. The separated crystals are filtered off, washed with a small amount of cold methanol and dried. 38 mg. (33%) of (±)-10-bromo-vincamine are obtained; m.p.: 220°-221° C. (from methanol).

IR (in KBr pellets): 1738 cm$^{-1}$ (ester CO).

$^1$H-NMR (CDCl$_3$): δ=7.68-6.85 (3H, m, aromatic protons), 4.50 (1H, replaceable, OH), 3.80 (3H, s, —COOCH$_3$), 0.89 (3H, t, —CH$_2$CH$_3$) ppm.

Mass spectrum: m/e (%)=432 (M$^+$, 100), 431 (47), 373 (56), 330 (89).

The mother liquor is purified by preparative thinlayer chromatography (adsorbent: aluminium oxide PF$_{254+366}$, solvent: a 100:1 mixture of dichloromethane and methanol), taking into account that the R$_f$ values decrease in the order of (±)-10-bromo-vincamine>(±)-10-bromo-14-epivincamine>unreacted (±)-10-bromo-14,15-dioxo-E-homo-eburnane. A 20:4 mixture of dichloromethane and methanol is applied as eluting solution, and the eluate is processed in a conventional way. In this way further 5 mg. of (±)-10-bromo-vincamine are obtained; thus the total yield of this compound amounts to 43 mg. (39%).

5 mg. (4%) of (±)-10-bromo-14-epivincamine are obtained as by-product; m.p.: 205°-206° C. (from methanol). Mass spectrum: m/e (%)=432 (M$^+$, 83), 431 (53), 385 (33), 373 (52), 330 (96).

EXAMPLE 16

(−)-1(S),12b(S)-9-Bromo-1-ethyl-1-(2'-methoxycarbonylethyl)-1,2,3,4,6,7,12,12b-octahydroindolo[2,3-a]quinolizine dibenzoyl-D-tartrate 1.4 g. (0.32 mmoles) of (±)-1α-ethyl-1β-(2'-methoxycarbonylethyl)-9-bromo-1,2,3,4,6,7,12,12bα-octahydroindolo[2,3-a]quinolizine are dissolved in 3 ml. of dichloromethane, and a solution of 1.19 g. of dibenzoly-D-tartaric acid in 7 ml. of dichloromethane is added. The reaction mixture is heated to boiling, and thereafter it is allowed to stand at room temperature for one hour and at +10° C. for additional 12 hours. The separated product is filtered off, washed with dichloromethane and dried. 0.82 g. (26%) of (−)-1(S),12b(S)-1-ethyl-1-(2'-methoxycarbonylethyl)-9-bromo-1,2,3,4,6,7,12,12b-octahydroindolo[2,3-a]quinolizine dibenzoyl-D-tartrate are obtained; m.p.: 153°-154° C., [α]$_D^{22}$=−98° (c=1, in dimethyl formamide).

$^1$H-NMR (CDCl$_3$): δ=0.9 (3H, t, —CH$_2$CH$_3$), 4.1 (1H, s, 12b-H), 7.3-7.6 (2H, Ar, Ar 10-11 H), 8.2-8.4 (1H, Ar 9-H) ppm.

The optical rotation power of the base liberated from the above salt is [α]$_D^{22}$=−101.9° ( c=0.726, in dichloromethane).

EXAMPLE 17

(−)-3(S),17(S)-10-Bromo-14-oxo-E-homo-eburnane 0.5 g. (0.65 mmoles) of (−)-1(S),12b(S)-1-ethyl-1-(2'-methoxycarbonylethyl)-9-bromo-1,2,3,4,6,7,12,12b-octahydroindolo[2,3-a]quinolizine dibenzoyl-D-tartrate are treated with a mixture of 5 ml. of dichloromethane and 2 ml. of 10% aqueous ammonia. The phases are separated from each other, the dichloromethane solution is dried over anhydrous sodium sulfate, filtered, and the filtrate is evaporated. 22 ml. of abs. toluene are added to the residue, and 2 to 3 ml. of the solvent are evaporated from the mixture at 107° C. The residual mixture is cooled to room temperature, 0.16 g. of lithium tert.-butoxide are added to it, and the mixture is stirred at room temperature for 60 hours. Thereafter a solution of 1.5 g. of ammonium chloride in 8 ml. of water is introduced, the mixture is stirred for 5 minutes, and the phases are separated from each other. The organic phase is washed with 10 ml. of water, dried over anhydrous sodium sulfate, filtered, and the filtrate is evaporated. The oily residue is dissolved in 2 ml. of benzene, and the solution is applied onto a column filled with a 100-fold amount of aluminium oxide (activity grade III) in benzene. The effluent is collected into fractions of 5 ml. each, and the individual fractions are analyzed by thin layer chromatography. The fractions containing the required product are combined and evaporated. The oily residue is dissolved in 1 ml. of dichloromethane, 5 ml. of ethanol are added to the solution, and the mixture is evaporated to a final volume of 1 ml. The separated crystals are filtered off, washed with ethanol and dried. In this way 0.12 g. (62%) of (−)-1(S),17(S)-10-bromo-14-oxo-E-homo-eburnane are obtained; m.p.: 121°–122° C., $[\alpha]_D^{20} = +26°$ (c=1, in dimethyl formamide).

$^1$H-NMR (CDCl$_3$): δ=7.3–7.55 (2H, Ar, 11–13 H), 8.4 (1H, Ar, 9-H), 4.1(1H, 3-H) ppm.

What we claim is:
1. A compound of the formula (XV)

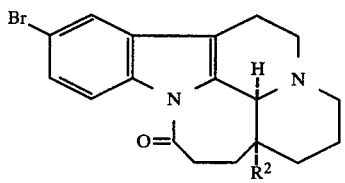

wherein $R^2$ is $C_1$ to $C_6$ alkyl, or a pharmaceutically acceptable acid addition salt thereof.

2. (±)-cis-10-bromo-14-oxo-E-homo-eburnane-(3αH,17αC$_2$H$_5$) or a pharmaceutically acceptable acid addition salt thereof as defined in claim 1.

3. A compound of the formula (XVI)

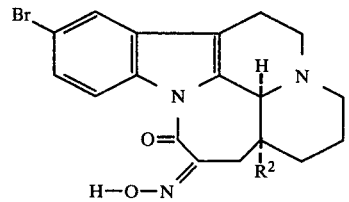

wherein $R^2$ is $C_1$ to $C_6$ alkyl, or a pharmaceutically acceptable acid addition salt thereof.

4. (±)-cis-10-bromo-14-oxo-15-hydroxyimino-E-homo-eburnane-(3αH,17αC$_2$H$_5$) or a pharmaceutically acceptable acid addition salt thereof as defined in claim 3.

5. A compound of the formula (XVII)

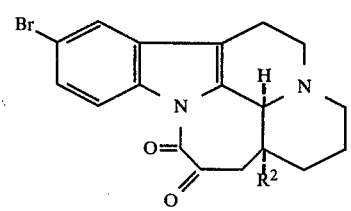

wherein $R^2$ is $C_1$ to $C_6$ alkyl, or a pharmaceutically acceptable acid addition salt thereof.

6. (±)-cis-10-bromo-14,15-dioxo-E-homo-eburnane or a pharmaceutically acceptable acid addition salt thereof as defined in claim 5.

* * * * *